(12) United States Patent
Cegla

(10) Patent No.: US 8,066,001 B2
(45) Date of Patent: Nov. 29, 2011

(54) THERAPEUTIC DEVICE

(75) Inventor: Ulrich Cegla, Montabaur (DE)

(73) Assignee: R. Cegla GmbH & Co. KG, Montabaur (DE)

( * ) Notice: Subject to any disclaimer, the term of this patent is extended or adjusted under 35 U.S.C. 154(b) by 909 days.

(21) Appl. No.: 12/080,556

(22) Filed: Apr. 3, 2008

(65) Prior Publication Data

US 2008/0251069 A1    Oct. 16, 2008

(30) Foreign Application Priority Data

Apr. 16, 2007  (DE) .......................... 10 2007 017 783

(51) Int. Cl.
- A61M 15/00 (2006.01)
- A61M 16/00 (2006.01)
- A62B 7/00 (2006.01)
- A62B 9/00 (2006.01)
- A62B 18/00 (2006.01)

(52) U.S. Cl. .................................... 128/200.24; 482/13

(58) Field of Classification Search ............. 128/200.24, 128/205.19, 204.24; 482/13, 10, 11; 600/538; 446/202, 207, 208, 209, 216, 416; 601/41, 601/38; 434/262, 268, 265, 272; 604/19

See application file for complete search history.

(56) References Cited

U.S. PATENT DOCUMENTS

| | | | | |
|---|---|---|---|---|
| 5,018,517 A | * | 5/1991 | Liardet | 128/200.24 |
| 5,569,122 A | * | 10/1996 | Cegla | 482/13 |
| 5,890,998 A | * | 4/1999 | Hougen | 482/13 |
| 6,984,214 B2 | * | 1/2006 | Fowler-Hawkins | 601/46 |
| 7,775,211 B2 | * | 8/2010 | Wilson | 128/848 |

FOREIGN PATENT DOCUMENTS

DE    4416575    11/1995

* cited by examiner

Primary Examiner — Justine Yu
Assistant Examiner — Colin W Stuart
(74) Attorney, Agent, or Firm — Pandiscio & Pandiscio

(57) ABSTRACT

In a therapeutic device (1) for assisting respiration, clearing of mucus and expectoration by a patient by means of which an oscillating air resistance can be generated in the air flow during exhalation and inhalation, with a mouthpiece (2) having an inlet opening (7) provided at one end of it and an elastically deformable hose piece (3) attached to its other end opposite to the inlet opening, it should be possible to adjust the respiration frequencies and pressure amplitudes for the individual patient during inhalation and exhalation. This is achieved in that a contact plate (21) is attached to the mouthpiece (2) and is aligned to run in parallel to the hose piece (3) in the area of the mouthpiece (2), that an articulating joint (22) is provided at the free end of the contact plate (21) by means of which a resistance body (23) is in an articulated connection with the contact plate (21), and that the resistance body (23) interacts with the section (5) of the hose piece (3) allocated to it in such a way that the passage area of the hose piece (3) can be variable adjusted from the outside.

10 Claims, 4 Drawing Sheets

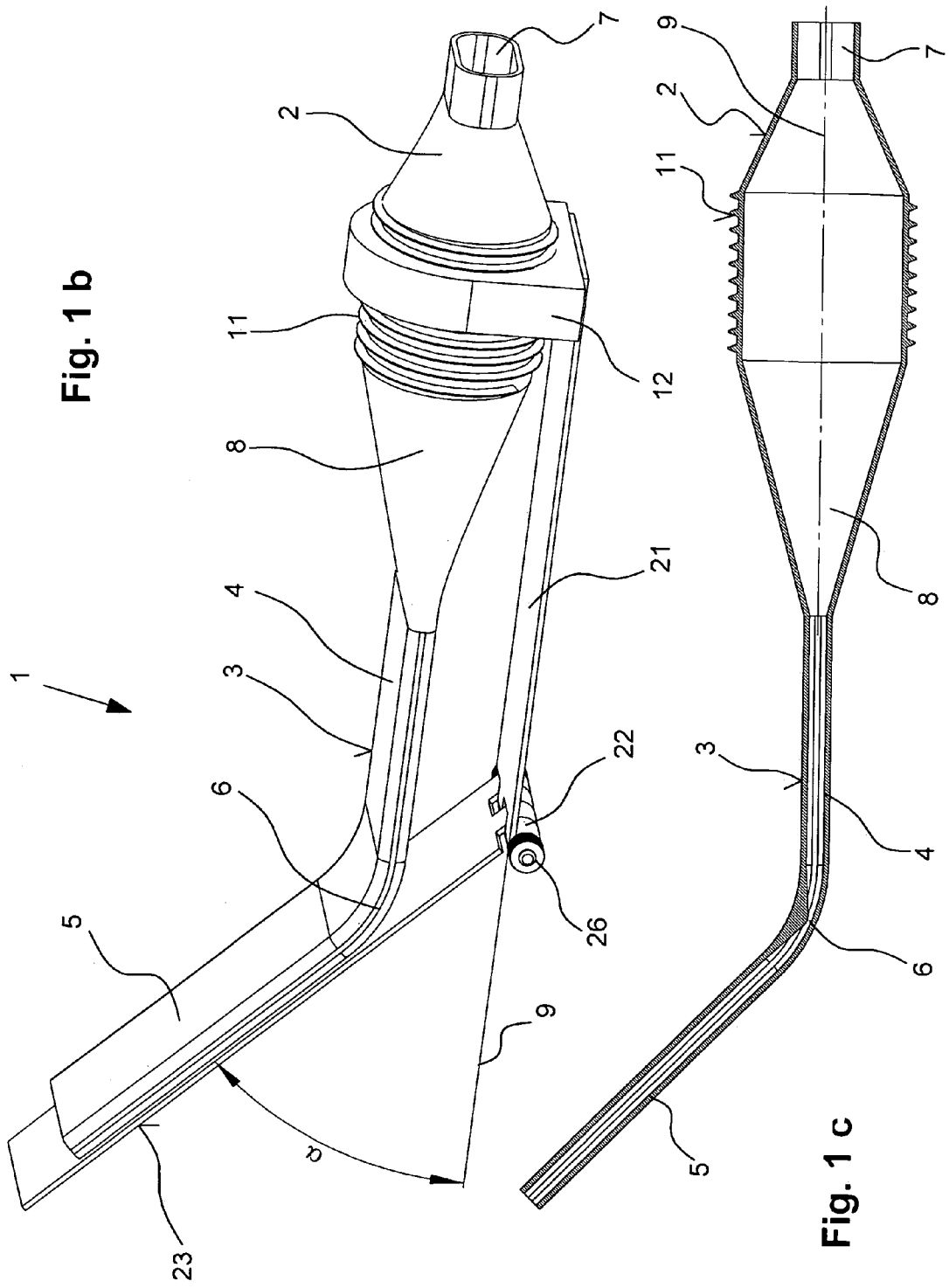

THERAPEUTIC DEVICE

Figure 1A:
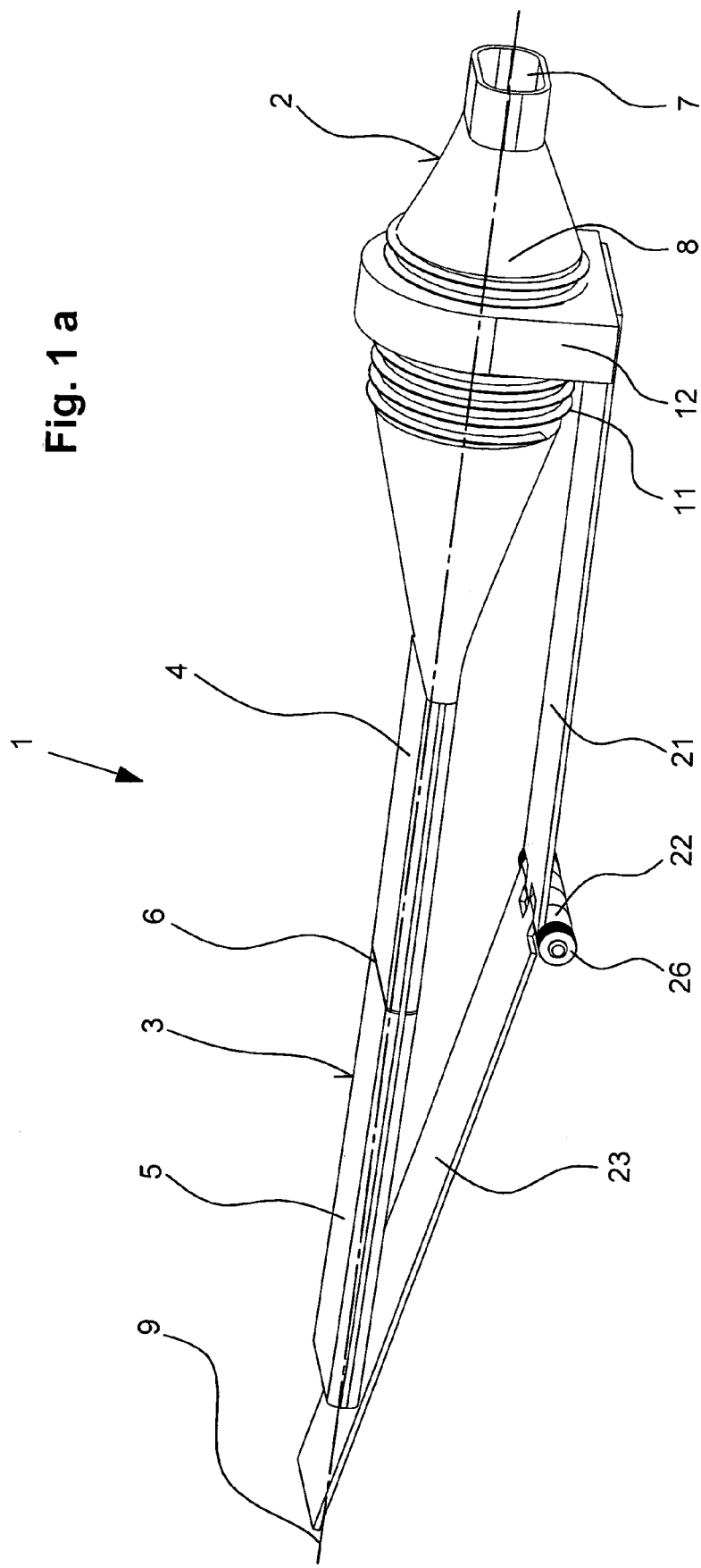

The present invention relates to a therapeutic device for assisting breathing, clearing of mucus and expectoration by a patient, by means of which an oscillating air resistance can be generated in the air flow during exhalation and inhalation, with a mouthpiece that has a passage opening provided at one of its ends and with an elastically deformable hose piece attached to its end opposite to the passage opening, or the present invention relates to a therapeutic device consisting of a mouthpiece that has a passage opening provided at one of its ends and with an elastically deformable hose piece attached to its end opposite to the passage opening, and that consists of a housing that is firmly attached to the mouthpiece and by means of which the hose piece is entirely or partially jacketed in the circumferential direction.

A therapeutic device is disclosed, for example, in DE 4416575 which principally comprises a housing curved in a quarter-circle profile into which the mouthpiece can be screwed. The hose piece is attached to the outlet from the mouthpiece and this hose piece is therefore in contact with the inside of the curved housing, in which case the hose piece is curved by the curvature of the housing. By turning the mouthpiece in the housing, the section of the hose piece that makes contact with the housing is increased or reduced depending on the direction of rotation of the mouthpiece. If, accordingly, the mouthpiece is screwed inwards in the direction of the housing, the section of the hose piece in contact with the inside wall of the housing increases and vice versa.

Inhaling and exhaling through the mouthpiece gives rise to an air flow which is therefore sucked in or blown out by the patient. The cross-sectional area of the hose piece, which is smaller in dimension than the cross-sectional area of the passage opening through the mouthpiece, establishes an air resistance by means of which human respiration is activated. In this way, it is intended for the periphery of the lungs to be treated in the event of complaints such as chronic bronchitis, bronchiectasis, cystic fibrosis, pulmonary emphysema and the like.

It has proven to be a disadvantageous feature of the therapeutic device of prior art that the air resistance occasioned by the hose piece can exclusively be set when the device is not being used, because patients have to take it away from their mouth in order to be able to adjust the mouthpiece.

Furthermore, it is disadvantageous that this adjustment only has an insignificant effect on reducing or increasing the air resistance, because the curvature of the housing provided in the therapeutic device does not achieve any significant change in angle or curvature of the hose piece. In order to treat respiratory problems, however, it is necessary to be able to adjust the pressure amplitudes and low-frequency vibrations so as to force the mucus that is to be cleared from the lung out of the lung by means of respiration. To achieve this, frequency changes and pressure differentials are required in order to promote fluctuations in the volumetric flow during the respiratory process.

The resonance frequency setting that the thoracic cage needs in order to overcome the air resistance during inhalation and exhalation is, based on experience, between 12 and 14 Hertz because this is the frequency at which the working effort required for exhalation and inhalation reduces, so that the therapeutic device can be used over a longer period of time. However, therapeutic treatment of this kind is not possible with the therapeutic device of prior art because the resonance frequency setting cannot be adjusted during inhalation and exhalation and therefore the patient is obliged to make the settings during intervals in respiration with the effect that achieving an exact setting individually adapted to each patient is impossible and also that it is not possible to vary the frequency during respiration.

Furthermore, the configuration of the therapeutic device of prior art suffers from the disadvantage that the fixed setting of the curvature in the housing wall only offers a specific and narrowly defined bandwidth of setting options for changing the air resistance.

It is therefore the task of the present invention to design a therapeutic device of the aforementioned kind which can be easily operated during the treatment of respiratory complaints such as cystic fibrosis, bronchiectasis, smoker's lung and the like and in which the respiratory frequencies and pressure amplitudes can be individually adjusted according to the patient's requirements during inhalation and exhalation within the widest possible range of applications.

In accordance with the present invention, this task is accomplished in that a contact plate is attached to the mouthpiece which is aligned in parallel to the hose piece in the area of the mouthpiece, that an articulating joint is attached to the free end of the contact plate by means of which a resistance body is articulated on the contact plate, and that the resistance body interacts with the area of the hose piece assigned to it in such a way that the cross section of the hose piece can be variably adjusted from the outside, or that a resistance body is attached to the housing in a movable articulated arrangement and located at a distance from the mouthpiece inside the housing, that the resistance body is provided as a support for a part of the free end of the hose piece and that the support enables the curvature of the hose piece to be adjusted.

Other advantageous further embodiments of the invention can be derived from the subordinate claims.

Due to the fact that the support bearing is accessible from the outside and can be moved into a specific angle position by means of the articulated joint or detent elements, the curvature of the hose piece can be adjusted within a wide range of angles with the effect that the air flow resulting in the hose piece can be adapted to the resonance frequency of the thoracic cage of the patient. As a result, the setting of the resonance frequency and pressure amplitude can be adjusted whilst the patient is inhaling and exhaling.

Once the optimum position for the resistance body has been found, the time during which the patient can use the therapeutic device is increased because the setting of the resonance frequency facilitates exhaling so that the patient can use the therapeutic device over a longer period without impairing the success of the treatment. In turn, this means that treatment successes can be achieved within a significantly shorter period of time because the patient will use the therapeutic device in accordance with the present invention more often and for a longer time.

Figure 2:
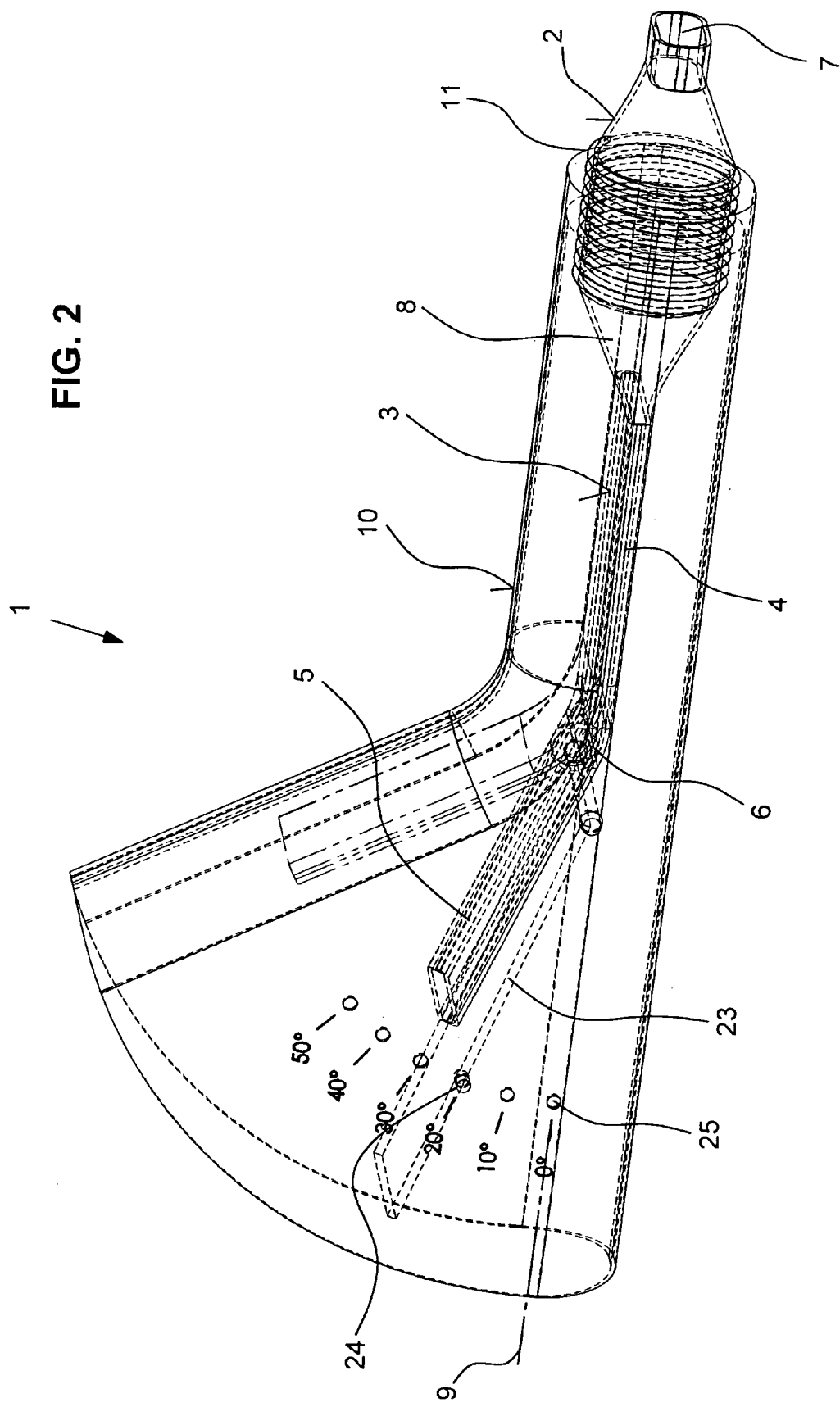
Figure 3:
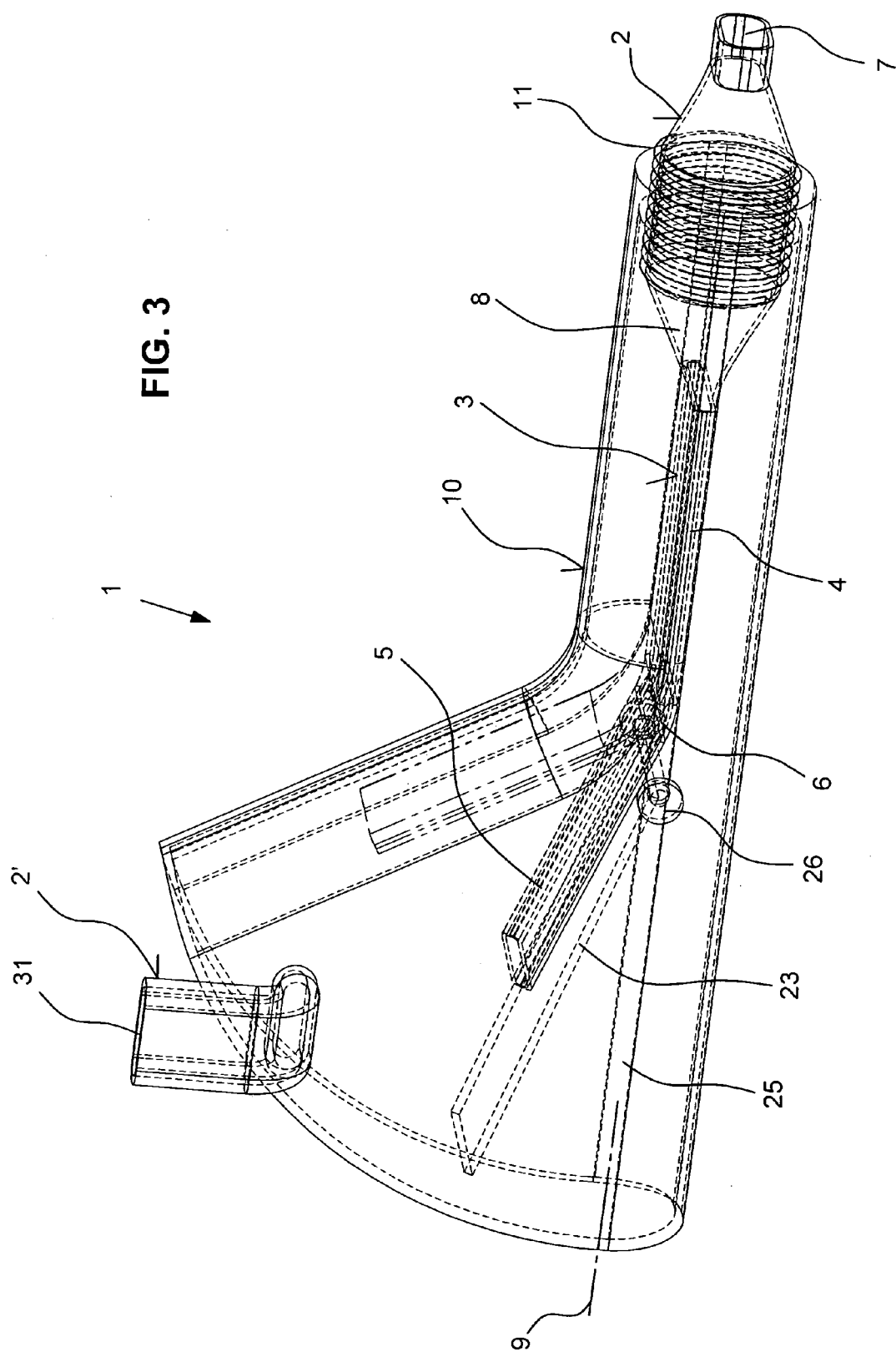

The drawing shows three sample embodiments configured in accordance with the present invention, the details of which are explained below. In the drawing, FIG. 1a shows a first sample embodiment of a therapeutic device comprising a mouthpiece and a hose piece that are attached to a contact plate, at the free end of which an articulated joint is provided for moving a resistance body, in a perspective view, FIG. 1b shows a sample embodiment of a therapeutic device in accordance with FIG. 1a with the resistance body in an elevated condition, FIG. 1c shows the therapeutic device in accordance with FIG. 1b, in section, FIG. 2 shows a second sample embodiment, in a perspective view and FIG. 3 shows a third sample embodiment of a therapeutic device comprising a mouthpiece with a hose piece attached to its end, and a housing which holds the mouthpiece and by which the hose piece is completely jacketed, and which has a resistance body in an articulated attachment in its interior, with a completely enclosed housing, in a perspective view.

FIGS. 1a, 1b, 1c, 2 and 3 show a therapeutic device 1 that is used for supporting the breathing, clearing of mucus and expectoration of a patient. The therapeutic device 1 consists of a mouthpiece 2 on which an inlet opening 7 is provided which can, for example, be inserted into the nasal or mouth openings of a patient. A passage channel 8 is worked inside the mouthpiece 2 and this opens out in the inlet opening 7.

Opposite to the end in which the inlet opening 7 is provided, there is a hose piece 3 that is firmly connected to the mouthpiece 2. The cross-sectional shape of the hose piece 3 in this case is rectangular. The passage duct 8 tapers in the direction of the hose piece so that the respiratory air flowing through the inlet opening 7 has to be forced through the duct 7 and the hose piece 3. This means an air flow is created in the hose piece 3 in particular by means of which the free end of the hose piece 3 is moved thereby resulting in an oscillating air resistance for the air flow through the hose piece 3 which is dependent on its length and cross-sectional area.

In order to allow the oscillating air resistance to be adapted to the individual characteristics of the patient, namely in order to achieve the resonance frequencies of the thoracic cage during inhalation and exhalation, the therapeutic device 1 in accordance with the present invention is equipped with a support plate 21 as shown in FIGS. 1a, 1b and 1c, in which case the support plate 21 is firmly connected to the mouthpiece 2 by means of a holding ring 12. The support plate 21 in this embodiment runs parallel to a first section 4 of the hose piece 3. The free end of the support plate 21 has an articulated joint 22 attached to it, by means of which a resistance body 23 is held in an articulated arrangement. The resistance body 23 interacts with a second section 5 of the hose piece 3.

In FIG. 1a in particular, it is possible to see that the resistance body 23 serves as a support for the second section 5 of the hose piece 3, because the hose piece 3 makes contact with the resistance body 23 in such a way that the two sections 4 and 5 of the hose piece 3 run in alignment with the longitudinal axis 9 of the therapeutic device 1 in this setting position. The cross-sectional area of the hose piece 3 is therefore unchanged over its complete length. During inhalation and exhalation by the patient, therefore, the respiratory air flows through the inside of the hose piece 3 without hindrance. The free end of the hose piece 3 flaps against the resistance body 23 and its movement is restricted to one side by this resistance body 23.

If the oscillation of the respiratory air created in this way fails to reach the resonance frequencies for the patient in question, the resistance body 23 can be moved to a specific angle position between 0° —corresponding to the position shown in FIG. 1a—and a deflection of 50°. The change in angle of the resistance body 23 in relation to the longitudinal axis 9 of the therapeutic device 1 causes the second section 5 of the hose piece 3 to be raised out of the longitudinal axis 9, as shown in FIGS. 1b and 1c, with the effect that a curved or kinked area 6 is formed between both sections 4 and 5 of the hose piece 3. The constant cross-sectional area over the entire length of the hose piece 3 is therefore reduced in the area of the kink 6 according to the selected angle position of the resistance body 23. This means if the resistance body 23 is moved out of the 0° to the 50° position then the cross-sectional area is at the largest in the 0° position and the passage area is at its smallest in the 50° position.

Consequently, the patent can individually adjust the position or angle position of the resistance body 23 during inhalation or exhalation, with the effect that the required resonance frequency can be adjusted during respiration. The articulated joint 22 is aligned in this case in such a way that it can be fixed using a setscrew 26 so that the position of the resistance body 23 is fixed in the selected angle position.

FIG. 2 shows the mouthpiece 2 screwed into a housing 10 with the result that the housing 10 completely jackets the hose piece 3. The contour of the housing 10 can be divided into two sections in this case, namely a round first section that runs in parallel to the first section 4 of the hose piece 3 and a second section that is assigned to the second section 5 of the hose piece.

The second section of the housing 10 in this case should have a trumpet or V-shape with the effect that the free end of the hose piece 3 can be moved between the resistance body 23 that is rotatably mounted on one or both side walls of the housing 10 and the inner wall of the housing 10 opposite to the resistance body 23. The end of the housing 10 is fully open in this case.

If the angle position of the resistance body 23 is moved in the direction of the inner wall of the housing 10 between which the hose piece 3 is arranged, the freedom of movement of the free end of the hose piece 3 is reduced to such an extent that the hose piece 3 flaps back and forth between the resistance body 23 and the inner wall of the housing located above it. The respiratory air flows out of the end of the housing 10 into the atmosphere.

The resistance body 23 has a spring detent projection 24 projecting in the direction of the side wall of the housing. Several holes 25 are worked into this side wall of the housing 10 and the detent projection 24 clips into them in order to lock the position of the resistance body 23 in a particular angle position.

Another adjustment option for achieving the resonance frequency of the therapeutic device 1 is provided by moving the mouthpiece 2 in the longitudinal direction 9 relative to the resistance body 23. In the sample embodiment shown in FIGS. 1a, 1b and 1c, the mouthpiece 2 is fixed in the holding ring 12 and in the sample embodiment shown in FIG. 2 the mouthpiece is screwed onto the housing 10. The change in position of the mouthpiece 2 is therefore assigned to the second section 5 of the hose piece 3 on the resistance body 23 to a greater or lesser degree, by means of which the resonance frequency of the hose piece 3 can also be changed.

Furthermore, turning the mouthpiece 2 causes the hose piece 3 to make contact with the resistance body 23 in various positions, thereby also making it possible to change the frequency of the air flow.

FIG. 3 shows the housing 10 entirely enclosed. An opening 31 is worked into a side wall of the housing 10 and a second mouthpiece 2' is inserted into this opening 31, by means of which the air can be sucked out of the inside of the housing 10. Therefore, a negative pressure is created inside the housing 10 during inhalation, and by this means an air flow is established through the hose piece 3 and the first mouthpiece 2. This air flow causes the hose piece 3 to flap, which therefore gives rise to an oscillating air resistance during inhalation.

The setscrew 26 is arranged outside the housing 10. This setscrew 26 provides a means both of adjusting the resistance body 23 and locking it in place.

The invention claimed is:

1. A therapeutic device (1) for assisting breathing, clearing of mucus and expectoration of a patient by generation of oscillating air resistance in the air flow during exhalation and inhalation, the device comprising a mouthpiece (2) having an inlet opening (7) provided at a first end thereof with an elastically deformable hose piece (3) attached to a second end thereof; a contact plate (21) attached to the mouthpiece (2) and aligned in parallel with a portion of the hose piece (3) attached to the mouthpiece (2); an articulating joint (22) attached to a free end of the contact plate (21); and a resistance body (23) adapted to be articulated on the contact plate (21), wherein the resistance body (23) interacts with a section (5) of the hose piece (3) such that a passage area of the hose piece (3) is variably adjustable from outside the device.

2. The therapeutic device in accordance with claim 1, wherein the resistance body (23) is movable in the direction of the hose piece (3) within an arc from 0° to 50° in relation to a longitudinal axis (9) of the therapeutic device.

3. The therapeutic device in accordance with claim 1, wherein the mouthpiece (2) is disposed in a housing (10) which encloses the hose piece (3) circumferentially and the end of the housing (10) opposite to the mouthpiece (2) is provided with a generally V-shaped passage opening; and the resistance body (23) is arranged in the passage opening.

4. The therapeutic device in accordance with claim 3, wherein a projection (24) is provided on the resistance body (23) projecting in the direction of one of two side walls of the housing (10), and at least one hole (25) is provided in the corresponding side wall of the housing, into which hole (25) the projection (24) is insertable in order to fix the resistance body (23) in a selected angle position.

5. A therapeutic device (1) for assisting breathing and expectoration of a patient by generation of oscillating air resistance in the air flow during inhalation and exhalation, the device comprising a mouthpiece (2) having an inlet opening (7) provided at a first end thereof and with an elastically deformable hose piece (3) attached to a second end thereof opposite to the inlet opening (7), and a housing (10) attached to the mouthpiece (2) and the hose piece (3) is circumferentially jacketed by the housing (10); wherein a resistance body (23) is attached to the housing (10) in a movable articulated arrangement via an articulating joint (22) and located at a distance from the mouthpiece (2) inside the housing (10), and the resistance body (23) is provided as a support for a section (5) of the hose piece (3), such that the support enables the curvature of the hose piece (3) to be adjusted.

6. The therapeutic device in accordance with claim 5, wherein during inhalation and exhalation, the hose piece (3) is movable in an oscillating fashion between the resistance body (23) and the inside wall of the housing (10).

7. The therapeutic device in accordance with claim 2, wherein the mouthpiece (2) together with the hose piece (3) can be moved in the longitudinal axis (9) to align it in relation to the resistance body (23).

8. The therapeutic device in accordance with claim 1, wherein the resistance body (23) is formed as a plate and the section (5) of the hose piece (3) is movable by the resistance body (23) when not being operated, into a level of elevation that is above or below a section (4) of the hose piece (3) attached to the mouthpiece (2).

9. The therapeutic device in accordance with claim 1, wherein the hose piece (3) is alignable in various angle positions in relation to the resistance body (23).

10. The therapeutic device in accordance with claim 5, wherein the housing (10) is a generally enclosed structure, and an opening (31) is disposed in a wall of the housing (10), and a second mouthpiece (2') is disposed in the opening (31).

\* \* \* \* \*